US008649010B2

United States Patent
Chen

(10) Patent No.: US 8,649,010 B2
(45) Date of Patent: Feb. 11, 2014

(54) INTEGRAL TRANSFORMED OPTICAL MEASUREMENT METHOD AND APPARATUS

(76) Inventor: Nanguang Chen, Singapore (SG)

(*) Notice: Subject to any disclaimer, the term of this patent is extended or adjusted under 35 U.S.C. 154(b) by 355 days.

(21) Appl. No.: 13/085,996

(22) Filed: Apr. 13, 2011

(65) Prior Publication Data

US 2011/0255863 A1    Oct. 20, 2011

Related U.S. Application Data

(60) Provisional application No. 61/323,938, filed on Apr. 14, 2010.

(51) Int. Cl.
*G06F 19/00*    (2011.01)
*G01N 21/00*    (2006.01)

(52) U.S. Cl.
USPC ............ 356/432; 356/433; 356/73.1; 324/96; 702/29

(58) Field of Classification Search
USPC ................................................. 356/436–442
See application file for complete search history.

(56) References Cited

U.S. PATENT DOCUMENTS 7,728,986 B2 * 6/2010 Lasker et al. ................. 356/497
2006/0178844 A1 * 8/2006 LeGore et al. ................. 702/29

OTHER PUBLICATIONS

Mo et al, "Fast time-domain diffuse optical tomography using pseudorandom bit sequences," Opt. Express, 16(18):13643-13650 (2008).
Zhang et al, "Three-dimensional scheme for time-domain fluorescence molecular tomography based on Laplace transforms with noise-robust factors," Opt. Express, 16(10):7214-7223 (2008).
Chen et al, "Time-resolved diffusive otical imaging using pseudorandom bit sequences," Opt. Express, 11(25):3445-3454 (2003).
Chen et al, "Time-resolved optical measurements with spread spectrum excitation," Optics Letters, 27(20):1806-1808 (2002).
Eda et al, "Multichannel time-resolved optical tomographic imaging system," Review of Scientific Instruments, 70(9):3595-3602 (1999).
Schmidt et al, "A 32-channel time-resolved instrument for medical optical tomography," Review of Scientific Instruments, 71(1):356-265 (2000).

* cited by examiner

*Primary Examiner* — Gregory J Toatley
*Assistant Examiner* — Rebecca C Bryant
(74) *Attorney, Agent, or Firm* — Ostrolenk Faber LLP

(57) ABSTRACT

An optical measurement method for high-speed acquisition of integral transformed time domain optical signals is presented. A circuit network is used to generate a modulation signal and a reference signal from a broadband signal such as a pseudo random bit sequence. The integral transformed measurements are obtained by cross correlating the time dependent response to the modulated illumination with the reference signal.

10 Claims, 2 Drawing Sheets

INTEGRAL TRANSFORMED OPTICAL MEASUREMENT METHOD AND APPARATUS

CLAIM OF PRIORITY

This application claims the benefit of U.S. Provisional Application Ser. No. 61/323,938, filed on Apr. 14, 2010 by the inventor, Nanguang Chen, the entire disclosure of which is incorporated by reference.

FIELD OF THE INVENTION

This invention relates to a method for direct measurement of integral transformed (e.g., Laplace transformed) optical signals. It can be used for high speed acquisition of time dependent optical signals for deriving bulk optical properties of the sample or reconstructing optical tomographic images.

BACKGROUND

Time-resolved measurement is frequently conducted to obtain more information than continuous measurement for optically characterizing various samples. In time-resolved fluorescence spectroscopy, the fluorescence from a sample is measured as a function of time after illumination by a flash of light such as the output from a pulsed laser. Fluorescence lifetime of certain molecules is a sensitive reporter on local microenvironment which is generally independent of fluorophores concentration and can be used as a means of discriminating between molecules with spectrally overlapping emission.

Diffuse optical tomography (DOT) is an emerging technology that uses diffusive photons to measure the optical properties and their spatial distribution in thick biological samples. In time-domain DOT systems the intensity of diffusive photons is measured as a function of time, which is termed as temporal point spread function (TPSF). It has been well accepted that time-domain DOT can provide improved image quality than continuous wave (CW) DOT systems, in which the static state light signal is measured. Conventional time-domain DOT system employs either a streak camera or time-correlated single photon counting (TCSPC) to record the TPSF of diffuse photons. A streak camera has high time-resolution around 1 picosecond. However, it is limited by low dynamic range and temporal nonlinearity. Although TCSPC provides high sensitivity, high dynamic range, and time-resolution, its data acquisition speed is generally very slow as a large number of photons need to be collected one by one to reduce statistic errors. Recently, Mo et al (Fast time-domain diffuse optical tomography using pseudorandom bit sequences, Opt. Express Vol. 16, 13643-13650) disclosed a spread spectrum time-resolve measurement method that is much faster than TCSPC and more suitable for clinical applications. In a spread spectrum time-resolved DOT system, the laser output is modulated either directly or using an external modulator by a pseudo-random bit sequence (PRBS). The modulated beam is irradiated on a sample under investigation. The detected diffusive photon density at a given distance is a function of time, which equals the convolution of the PRBS with the TPSF. Cross-correlation between the PRBS and the detected signal yields an approximate measurement of the original TPSF at a specific time delay. Such an operation is implemented by the use of hardware devices such as a mixer and a low pass filter. A programmable delay line is used to shift the relative time delay between the PRBS and the detected signal so that the whole time spectrum is obtained point by point.

Image reconstruction in DOT is a process of generating maps of optical properties using the measured optical signals such as TPSFs. Usually it is computationally expensive if the TPSFs are directly used as input to the reconstruction algorithms due to the huge amount of measurement data. In practice, the TPSFs are pre-processed by using a variety of transforms to retrieve the essential information. The frequently used integral transforms include Laplace transform and Fourier transform. It has been demonstrated that Laplace transform with only a pair of transform parameters lead to uncompromised image quality (Zhang et al 2008, Three-dimensional scheme for time-domain fluorescence molecular tomography based on Laplace transforms with noise-robust factors, Opt. Express Vol. 16, 7214-7223). The advantages of using Laplace transformed data include simplified mathematical models, significantly reduced computation time, and low sensitivity to noises.

SUMMARY AND OBJECTIVES OF THE INVENTION

It is the objective of the present invention to further improve the data acquisition speed and signal to noise ratio for time-domain optical measurement systems, especially time-domain DOT systems.

It is another objective of the present invention to reduce the complexity, cost, and size of time-domain optical measurement systems, especially time-domain DOT systems.

The objectives are achieved by a method for generation of integral transformed time domain measurements that includes generating a broadband signal, generating a modulation signal and a reference signal from the broadband signal using a circuit network, illuminating a sample with a light source modulated by the modulation signal, and cross-correlating the detected signal from the sample with the reference signal.

The circuit network for generation of the modulation and reference signals includes filters. When a first order low pass filter is used to generate either a modulation signal or a reference signal, the time domain measurement is Laplace transformed. The time constant of the filter determines the transform parameter.

Other features and advantages of the present invention will become apparent from the following description of the invention which refers to the accompanying drawings.

DETAILED DESCRIPTION OF EMBODIMENTS OF THE INVENTION

Figure 1:
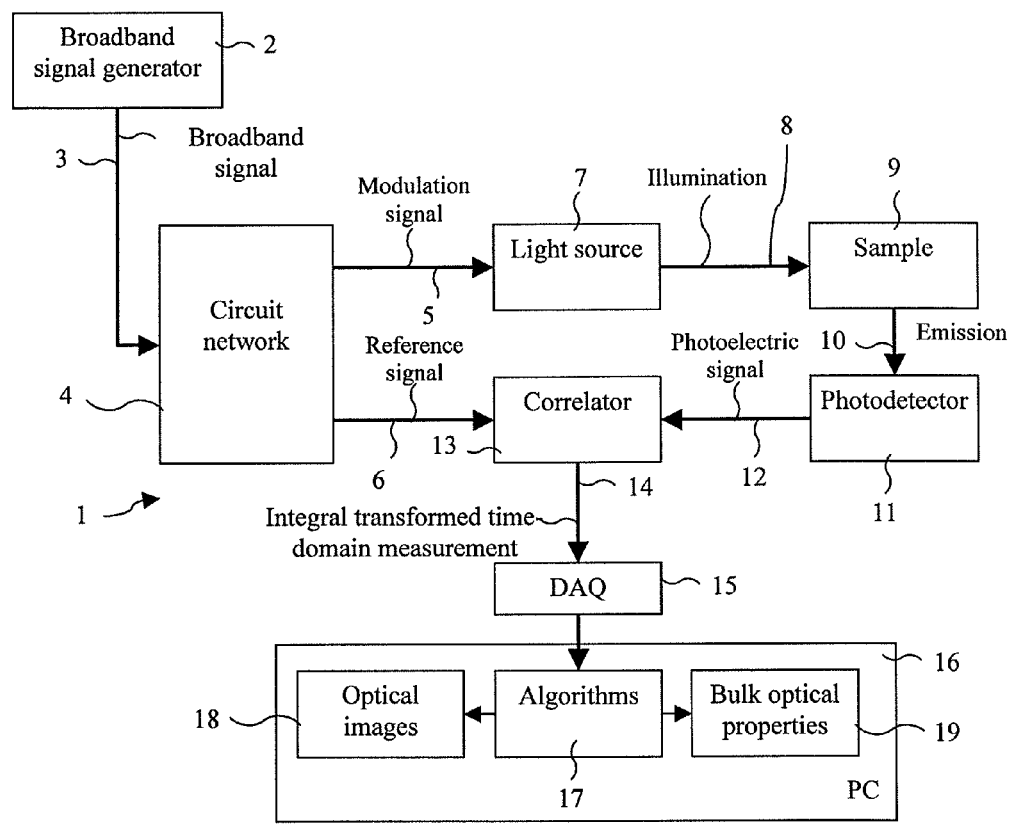
FIG. 1 schematically illustrates an optical measurement apparatus implementing a method according to the present invention.

FIG. 1 schematically shows the design of an optical measurement apparatus 1 implementing a method according to the present invention. A broadband signal generator 2 generates a broadband signal 3, which has a narrow spike autocorrelation function, or an autocorrelation function similar to a delta function. In signal processing, the autocorrelation of a periodic function $f(t)$ is defined as, $$R_{ff}(\tau) = \frac{1}{T}\int_0^T f(t)f(t+\tau)dt$$

where T is the signal period and τ is the time delay. For non-periodic signals, the above equation can be generalized to compute the limit as T approaches infinity. When the power spectrum of ƒ (t) in the frequency domain is broad, its autocorrelation function jumps to the peak value around τ=0, ±T, ±2T, ... but is essentially zero elsewhere. A practical choice of the broadband signal is PRBS, which can be reliably generated with linear feedback shift registers. The broadband signal 3 passes through a circuit network 4 to generate a modulation signal 5 and a reference signal 6. The modulation signal 5 is used to modulate the intensity of a light source 7, whose optical output 8 illuminates a sample 9 under investigation. The light sources 7 can be a VCSEL (vertical cavity surface emitting laser diode), which can be directly modulated at a high bit rate greater than 1 Gb/s. Alternatively the light source 7 can be a laser coupled to an external intensity modulator such as a Mach-Zehnder modulator or an electro-optical modulator. In response to the illumination 8, the sample 10 emits various types of optical signals including reflectance, transmittance, and fluorescence. A specific type of the emissions is collected by the photodetector 11 that converts the light signal to a photoelectric signal 12, which is time dependent. The photodetector 11 should contain at least a high-speed light detector such as a semiconductor detector (e.g., photodiode and avalanche photodiode), or a photomultiplier tube (PMT). Broadband amplifiers may be included to enhance the signal level. The correlator 13 performs cross correlation for two input signals. A typical implementation of the correlator comprises an analog multiplier and a low pass filter. The cross correlation between the photoelectric signal 12 and the reference signal 6 yields the integral transformed time domain optical measurement 14, which is digitized by a data acquisition (DAQ) device 15 and transferred to a personal computer (PC) 16. Multiple measurements can be obtained by using multiple light sources and/or multiple detectors, or scanning the light source or detector mechanically over the sample 10. Various reconstruction algorithms 17 on the PC 16 can be used to translate the integral transformed time domain optical measurements to optical images 18 and/or bulk optical properties 19.

Figure 2:
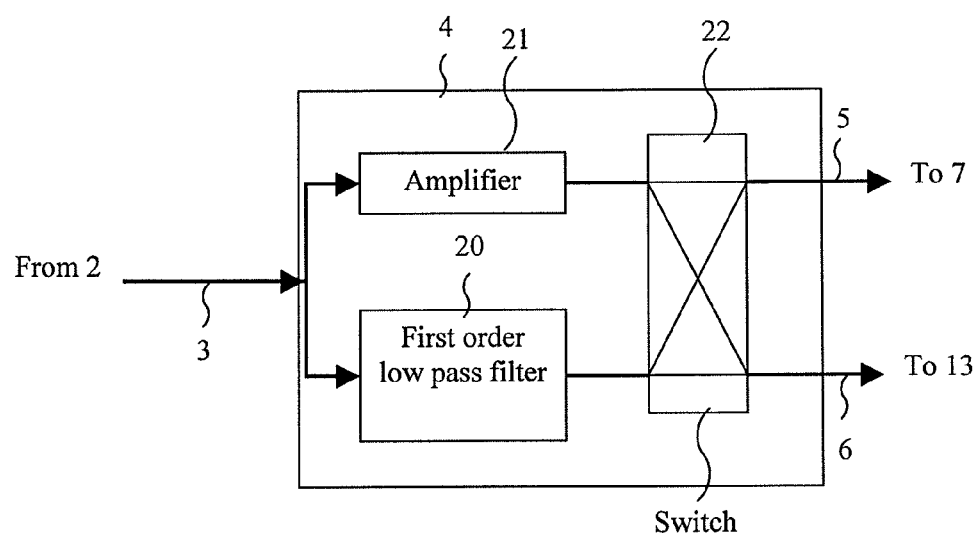
FIG. 2 is a schematic representation of an example of a circuit network as used in the optical measurement apparatus of FIG. 1.

The exact form of integral transform is determined by the configuration of the circuit network 4. FIG. 2 shows an example design of the circuit network 4, which comprises a first order low pass filter 20, a broadband amplifier 21, and a switch 22. The switch 22 is used to selectively connect the outputs of the filter 20 and the amplifier 21 to the light source 7 or the correlator 13. In case that the output of the amplifier is connected to the light source 7 and the output of the filter is connected to the correlator 13, the modulation signal 5 is a copy of the broadband signal 3 with approximately the same frequency spectrum shape. If the broadband signal 3 is strong enough, the amplifier 21 can be bypassed or even replaced by an attenuator. The reference signal 6 is the convolution of the broadband signal 3 with the impulse response of the filter 20, which is an exponential function of time. With such a configuration, the integral transform becomes a Laplace transform. The corresponding Laplace transform parameter is simply the reciprocal of the time constant of the filter 20. In case that the output of the amplifier 21 is connected to the correlator 13 and the output of the filter 20 is connected to the light source 7, the integral transform is still a Laplace transform if the relative time delay between the two signals 5 and 6 is appropriately adjusted. However, the sign of the Laplace transform parameter is reversed in this case. The filter 20 can be implemented as an analog filter or a digital filter and its time constant can be either fixed or adjustable.

As described in above embodiments, the Laplace transformed time domain optical measurements with real (positive and negative) transform parameters can be obtained directly using hardware. There is no need to record the time spectrum point by point and perform the Laplace transform numerically. Hence, the data acquisition time is significantly reduced with this inventive method. One the other hand, the signal to noise ratio can be improved if the same data acquisition time is used.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for measuring integral transformed optical signals, comprising of the steps of:
   a. generating a broadband signal;
   b. generating a modulation signal and a reference signal by passing said broadband signal through a waveform shaping circuit network;
   c. intensity modulating a light source using said modulation signal;
   d. illuminating a sample using the output of said light source;
   e. converting the emission from said sample to a time dependent photoelectric signal using a photodetector; and
   f. cross correlating said time dependent photoelectric signal with said reference signal using a correlator to obtain integral transformed time domain measurements of said emission, wherein said circuit network comprises a first order low pass filter, and wherein said modulation signal or said reference signal generated in step b) is a convolution of the broadband signal with an impulse response of the first order low pass filter.

2. The method of claim 1, wherein said broadband signal is a pseudo random bit sequence.

3. The method of claim 1, wherein said correlator comprises an analog multiplier and a low-pass filter.

4. The method of claim 1, comprising the further step of reconstructing the optical images of said sample using said integral transformed time domain measurements.

5. The method of claim 1, comprising the further step of estimating the optical properties of said sample using said integral transformed time domain measurements.

6. The method of claim 1, wherein said broadband signal has a narrow spike correlation function.

7. The method of claim 1, wherein said broadband signal has an autocorrelation function similar to a delta function.

8. The method of claim 1, wherein said waveform shaping circuit network further includes an amplifier and a switch, and wherein said switch can selectively connect output of said filter to the correlator or to said light source, and selectively connect output of said amplifier to said correlator or to said light source.

9. A method for measuring integral transformed optical signals, comprising of the steps of:
  a. generating a broadband signal;
  b. generating a modulation signal and a reference signal by passing said broadband signal through a waveform shaping circuit network;
  c. intensity modulating a light source using said modulation signal;
  d. illuminating a sample using the output of said light source;
  e. converting the emission from said sample to a time dependent photoelectric signal using a photodetector; and
  f. cross correlating said time dependent photoelectric signal with said reference signal using a correlator to obtain integral transformed time domain measurements of said emission; wherein
  said waveform shaping circuit network includes a first order low pass filter, an amplifier, and a switch, and wherein said switch can selectively connect output of said filter to the correlator or to said light source, and selectively connect output of said amplifier to said correlator or to said light source.

10. The method of claim 9, wherein said modulation signal or said reference signal generated in step b) is a convolution of the broadband signal with an impulse response of said first order low pass filter.

* * * * *